United States Patent
Neelwarne et al.

(10) Patent No.: US 6,849,453 B2
(45) Date of Patent: Feb. 1, 2005

(54) METHOD AND COMPOSITION FOR CLONAL PROPAGATION OF *PANDANUS AMARYLLIFOLIUS*

(75) Inventors: Bhagyalakshmi Neelwarne, Mysore (IN); Thimmaraju Rudrappa, Mysore (IN); Mandayam Singara Narayan, Mysore (IN); Gokare Aswathanarayana Ravishankar, Mysore (IN)

(73) Assignee: Council of Scientific & Industrial Research, New Delhi (IN)

( * ) Notice: Subject to any disclaimer, the term of this patent is extended or adjusted under 35 U.S.C. 154(b) by 9 days.

(21) Appl. No.: 10/400,308

(22) Filed: Mar. 27, 2003

(65) Prior Publication Data

US 2004/0191908 A1 Sep. 30, 2004

(51) Int. Cl.⁷ ................................................. C12N 5/00
(52) U.S. Cl. ....................................................... 435/410
(58) Field of Search .......................................... 435/410

(56) References Cited

PUBLICATIONS

M. Apintanapong et al. "The use of spray drying to microencapsulate 2–acetyl–1–pyrroline, a major flavour component of aromatic rice," International Journal of Food Science and Technology, Feb. 2003, © 2003 Blackwell Publishing Ltd., Online Publication Date: Jan. 15, 2003, vol. 38, Issue 2, pp. 95–102.

Pandanus (*Pandanus amaryllifolius* Roxb.) via Internet at http://www–ang.kfunigraz.ac.at/~katzer/engl/Pand_ama.html, Printout Date: Aug. 24, 2004, Modification Date: Sep. 12, 2001, pp. 1–8.

*Primary Examiner*—Bruce R. Campbell
*Assistant Examiner*—S. B. McCormick-Ewoldt
(74) *Attorney, Agent, or Firm*—Ross Spencer Garsson Winstead Sechrest & Minick, P.C.

(57) ABSTRACT

The present invention provides a method of clonal propagation of *Pandanus amaryllifolius* and further provides a composition for the clonal propagation of scented *Pandanus amaryllifolius*.

8 Claims, No Drawings

METHOD AND COMPOSITION FOR CLONAL PROPAGATION OF *PANDANUS AMARYLLIFOLIUS*

FIELD OF THE INVENTION

The present invention relates to a method of clonal propagation of *Pandanus amaryllifolius*. The present invention relates to a composition for the clonal propagation of scented *Pandanus amaryllifolius*.

BACKGROUND ART

*Pandanus amaryllifolius* is a member of the family Pandanaceae comprising a group of plants generally known as 'screw pines'. Earlier studies by Buttery et al (Chem. Ind. London, Vol. 23, page 478 of year 1982) indicated that 2-acetyl-1-pyrroline is the major flavour constituent of *Pandanus* leaves, while other constituents like volatile oils, alcohols, aromatic aldehydes, ketones and esters were also traceable. The major compound, 2-acetyl-1-pyrroline, has commercial significance as a major flavour constituent that impart the characteristic aroma of scented rice varieties such as Basmati rice of India, 'Khao Dawk Mali-105' of Thailand and Kaorimai of Japan. The essential oil of *Pandanus* is known to impart 10-times more flavour than the highly scented rice and 100-times more than that present in normal rice (Chem. Ind. London, Vol. 23, page 478 of year 1982). *Pandanus* extract has been reported to possess anti-oxidant properties. *Pandanus* leaf is cited as an ingredient in many Indian, Thai and Indonesian recipes. *Pandanus amaryllifolius* is not known to grow in wild state whereas the plants are grown as ornamentals in pots or grown in kitchen gardens in parts of South East Asia, Indonesia and New Guinea. The plant produces only 6–8 suckers per year and is known to produce male flowers only in New Guinea. Female flowers are not known in the variety that synthesizes aroma in the leaves. Thus the lack of its wild population or the large-scale cultivation on one hand and a high potential for its economic importance on the other hand indicate a huge future demand for this plant material. Thus there could be possibilities of its organized cultivation and hence would be a demand for the planting material. To meet such demands, a method for rapid production of plantlets by tissue culture means has tremendous scope. Since the flavor compound in this plant is known to vary in each variety, the plant material with highest perceivable flavor level was selected and a method for rapid multiplication of plantlets was invented.

Plant Tissue Culture (PTC) is a major area of plant biotechnology, which has direct impact on present day agriculture/horticulture. The need for enormous supply of desired type of planting/sowing material may be obtained by applying tissue culture method as an alternative to conventional method. At present, several laboratories in the world are producing over 650 million plants annually, by applying tissue culture method.

There are various advantages of tissue culture (TC) plants over those produced by conventional methods of plant propagation. As TC plants are produced in completely controlled environment, the chances of carrying systemic diseases are rare. The plants are induced to multiply at a tremendous rate by developing specific medium formulation for each plant material. Maximum number of plants can be produced using minimum space, time and nutrients. Similarly, storage and transportation can be handled with lesser cost than for conventional plants. It facilitates the availability of planting material throughout the year.

The present invention relates to a medium formulation for the clonal propagation of scented *Pandanus amaryllifolius* Roxb. wherein the development of specific nutrient medium with growth regulators help establishment of shoot cultures and rapid further aseptic multiplication of *Pandanus* shoots which may subsequently be hardened to obtain high quality *Pandanus* planting material.

There are no reports on the tissue culture studies or clonal propagation of *Pandanus amaryllifolius*. However there are certain studies on the chemical composition of the plant at different stages of its life cycle.

Laksanamai V. and Ilangantilake S. (Cereal Chemistry Vol. 70 (4) 1983) found 2-acetyl-1-pyrroline in *Pandanus* leaves at levels 1 ppm (on fresh weight basis) and described this aroma as that present in scented rice varieties.

Another flavour, ethyl formamide present in rice as a flavouring compound has been identified in *Pandanus* leaves (Naturwissenchaften, Vol. 71: 215, 1984). Yet another study found 3-methyl-2-(5H)-furanone as the main volatile compound in *Pandanus* leaves, besides 3-hexanol, 4-methylpentanol, 3-hexanone and 2-hexanone (Flavour Chemistry of ethnic foods—Proceedings of a Meeting held during the $5^{th}$ Chemical Congress of North America, Cancun, Nov. 11–15, 1997 (1999)).

The drawback associated with the methods followed hitherto for the supply of planting material is that of the conventional type of propagation involves injury to the mother plant for collecting the lateral shoot suckers which is often associated with the sacrificing of the selected high yielding mother plant. Conventional method of propagation transmits systemic infection present in the mother plant acquired from one generation to the next leading to diseased planting material. The rate of multiplication is slow.

OBJECTS OF THE PRESENT INVENTION

The main object of the present invention is to provide a method for the micro-propagation of scented *Pandanus amaryllifolius* through tissue culture.

An object of the present invention is to provide a method for the establishment of aseptic shoot cultures of *Pandanus* using both terminal and lateral shoot buds as explants and using tissue culture methods.

Yet another object of the present invention is to provide a method to use suitable tissue culture medium for the micro propagation of scented *Pandanus amaryllifolius* under controlled propagation conditions.

Still yet another object of the present invention is to provide method for *Pandanus* plantlet production for the exchange and conservation of disease-free *Pandanus* germplasm.

It is also an object of the present invention is to provide a composition congenial for the micro-propagation of *Pandanus*, which obviates the drawbacks as detailed above.

Further object of the present invention is to provide a nutrient composition for the establishment of aseptic shoot cultures of *Pandanus* using both terminal and lateral shoot buds as explants and using tissue culture methods.

Yet another object of the present invention is to provide the most suitable composition as well as growth regulators composition for maximum multiplication of shoot cultures.

Still yet another object of the present invention is to provide the best combination of light and temperature conditions for maximizing the multiplication of the shoot cultures using the proposed culture medium.

Further object of the present invention is to provide the nutrient requirements for the development of roots from micro-propagated shoot cultures to facilitate easy establishment of *Pandanus* plantlets when transferred to soil.

SUMMARY OF THE INVENTION

The present invention also relates to a method of clonal propagation of *Pandanus amaryllifolius*. The present invention also provides a composition for the clonal propagation of scented *Pandanus amaryllifolius*.

DETAILED DESCRIPTION OF THE INVENTION

Accordingly, the present invention provides a method for the micro-propagation of scented *Pandanus amaryllifolius* through tissue culture, said method comprising the steps of:

(a) cutting one or more plant explants of *Pandanus amaryllifolius*;

(b) removing any soil and other contaminants from the surface of the explants;

(c) cutting the decontaminated explants in laminar flow;

(d) culturing the explants for three—eight weeks is at 20–35 degree C. in dark in a medium consisting of following ingredients $NH_4NO_3$, in the range of 750–2000; $KNO_3$, 800–1800; $H_3BO_4$, 6.2; $KH_2PO_4$, 170.0; KI, 0.83; $Na_2MoO_4$, 0.25; $CoCl_2$, 0.025; $CaCl_2$ $2H_2O$, 440–800; $MgSO_4$ $7H_2O$, 370.00; $MnSO_4$ $4H_2O$, 22.30; $MnSO_4$ 4 $H_2O$, 22.30; $ZnSO_4$, 8.60; $CuSO_4$ $5H_2O$, 0.025; $Na_2$ EDTA, 37.35; $FeSO_4$ $7H_2O$, 27.85; Thiamine HCl, 1.00; Pyridoxine HCl, 1.00; Nicotinic acid, 1.00; Glycine, 4.00; Inositol, 100.00; Ascorbic acid, 50.00–250.00; Glutamine, 50–200; Sucrose, 10000–40000; Soluble polyvinyl pyrrolidone 500–4000; Benzyl amino purine, 0.01–2.0; gellan gum GELRITE™ PHYTAGEL™, 2000.00, added in weight as milligrams and the final volume made up to one liter by adding glass distilled water at a pH in the range of 5.4 to 6.2 and sterilized by autoclaving, to obtain organized shoot bud/shoot, (e) continuing the culture of the explants until organized shoot buds/shoots are formed;

(f) harvesting the shoot buds/shoots thus formed;

(g) culturing the shoots as (f) in a second medium consisting of following ingredients $NH_4NO_3$, in the range of 1000–2500, $KNO_3$, 500–2000; $H_3BO_4$, 6.2; $KH_2PO_4$, 170.0; KI, 0.83; $Na_2MoO_4$, 0.25; $CoCl_2$, 0.025; $CaCl_2$ $2H_2O$, 440.00; $MgSO_4$ $7H_2O$, 370.00; $MnSO_4$ $4H_2O$, 22.30; $MnSO_4$ 4 $H_2O$, 22.30; $ZnSO_4$, 8.60; $CuSO_4$ $5H_2O$, 0.025; $Na_2$ EDTA, 37.35; $FeSO_4$ $7H_2O$, 27.85; Thiamine HCl, 1.00; Pyridoxine HCl, 1.00; Nicotinic acid, 1.00; Glycine, 4.00; Inositol, 100.00; Ascorbic acid, 50.00–250.00; Sucrose, 10000–30000.00; Kinetin, 0.02–4.0; Benzyl amino purine, 0.5–5.0; Agar, 7000.00–12000, added in weight as milligrams and the final volume made up to one liter by adding glass distilled water: at 20–35 degree C. in the presence of cool white light of about 1500–6000 lux of 16 hour photoperiod for about three to six weeks, at a pH in the range of 5.4 to 6.2 and sterilized by autoclaving to induce multiple shoots;

(h) transferring the small clusters back to the second medium to propagate shoots;

(i) transferring the elongated shoots to a third medium comprising about 50% of the salts of the second medium without growth regulator and 30–80% sucrose of the second medium, all dissolved in tap water, at a pH in the range of 5.4 to 6.2, 10000 mg per liter of agar and sterilized by autoclaving; and (j) culturing the shoots of step (i) at about 20–35 degree C. in the presence of cool white light of about 1500–6000 lux of 16 hour photoperiod for at least three weeks, to induce roots and to partially harden the individual shoots and further to obtain a large number of partially hardened shoots by tissue culture for transferring to the soil.

Yet another embodiment of the present invention, wherein the plant explants are selected form axillary/terminal shoot tips/buds of *Pandanus amaryllifolius* plants.

Further embodiment of the present invention, wherein at least one plant growth regulator that is employed in the medium of step (d) and step (g) is selected from the group consisting of auxins and cytokinins, and a combination thereof.

Still another embodiment of the present invention, wherein the growth regulator auxin is selected from the group consisting of indole acetic acid, indole butyric acid and naphthalene acetic acid, at a concentration range varying between 0.01 to 10 mg/L w/v. It is also an embodiment of the present invention, wherein the growth regulator cytokinins is selected from the group consisting of 6-benzylamino-purine, gamma-gamma-dimethyl allylamino purine, isopentinyl adenine and kinetin, at a concentration range varying between 0.01 mg/L up to 20 mg/L.

Yet another embodiment of the present invention, wherein the decontamination of the small tissue is achieved by dipping in a solution containing at least one sterilizing agent selected from the group consisting of sodium hypochlorite, calcium hypochlorite, mercuric chloride, and ethyl alcohol.

Yet another embodiment of the present invention, wherein said method facilitates shoot multiplication to the extent of 10 fold in about 4 weeks time period.

Still another embodiment of the present invention, wherein said method facilitates production of *Pandanus amaryllifolius* plantlets free from saprophytic, fungal and bacterial diseases.

Further embodiment of the present invention, wherein explants from *Pandanus* shoot axis are surface sterilized, aseptically dissected in laminar air-flow and meristems/shoot buds are isolated for transfer to Murashige and Skoog's tissue culture medium with 3% w/v of sucrose as the carbon source and various combinations of growth regulators for shoot bud establishment.

In another embodiment of the present invention the cultured shoot buds are subjected for shoot multiplication using Murashige and Skoog's nutrient medium with changes in the concentrations of growth regulators to induce multiple shoot cultures.

In yet another embodiment of the present invention, the multiple shoots may aseptically be transferred to yet another Murashige and Skoog's medium with reduced levels of nutrients to induce roots helpful for subsequent transfer of the plantlets to soil.

Yet another embodiment of the present invention, wherein the decontamination of the small tissue is achieved by dipping in a solution containing at least one sterilizing agent selected from the group consisting of sodium hypochlorite, calcium hypochlorite, mercuric chloride, and ethyl alcohol.

In an embodiment of the present invention explants from *Pandanus* shoot axis are surface sterilized, aseptically dissected in laminar air-flow and meristems/shoot buds are isolated for transfer to Murashige and Skoog's tissue culture medium with 3% w/v of sucrose as the carbon source and various combinations of growth regulators for shoot bud establishment.

In another embodiment of the present invention the cultured shoot buds are subjected for shoot multiplication using Murashige and Skoog's nutrient medium with changes in the concentrations of growth regulators to induce multiple shoot cultures.

In yet another embodiment of the present invention, the multiple shoots may aseptically be transferred to yet another Murashige and Skoog's medium with reduced levels of nutrients to induce roots helpful for subsequent transfer of the plantlets to soil.

The present invention also provides composition for inducing multiple shoots for the micro-propagation of scented *Pandanus amaryllifolius*, said composition comprising: $NH_4NO_3$, in the range of 750–2000, $KNO_3$, 800–1800; $H_3BO_4$, 6.2; $KH_2PO_4$, 170.0; KI, 0.83; $Na_2MoO_4$, 0.25; $CoCl_2$, 0.025; $CaCl_2$ $2H_2O$, 440–800; $MgSO_4$ $7H_2O$, 370.00; $MnSO_4$ $4H_2O$, 22.30; $MnSO_4$ $4H_2O$, 22.30; $ZnSO_4$, 8.60; $CuSO_4$ $5H_2O$, 0.025; $Na_2$ EDTA, 37.35; $FeSO_4$ $7H_2O$, 27.85; Thiamine HCl, 1.00; Pyridoxine HCl, 1.00; Nicotinic acid, 1.00; Glycine, 4.00; Inositol, 100.00; Ascorbic acid, 50.00–250.00; Glutamine, 50–200; Sucrose, 10000–40000; Soluble polyvinyl pyrrolidone 500–4000; Benzyl amino purine, 0.01–2.0; GELRITE-™ (phytagel), 2000.00 all added in weight as milligrams and the final volume made up to one liter by adding glass distilled water. An embodiment of the present invention, a composition for inducing multiple shoots for the micro-propagation of scented *Pandanus amaryllifolius*, said composition comprising: $NH_4NO_3$, in the range of 1000–2500, $KNO_3$, 500–2000; $H_3BO_4$, 6.2; $KH_2PO_4$, 170.0; KI, 0.83; $Na_2MoO_4$, 0.25; $CoCl_2$, 0.025; $CaCl_2$ $2H_2O$, 440.0 $MgSO_4$ $7H_2O$, 370.00; $MnSO_4$ $4H_2O$, 22.30; $MnSO_4$ $4H_2O$, 22.30; $ZnSO_4$, 8.60; $CuSO_4$ $5H_2O$, 0.025; $Na_2$ EDTA, 37.35; $FeSO_47H_2O$, 27.85; Thiamine HCl, 1.00; Pyridoxine HCl, 1.00; Nicotinic acid, 1.00; Glycine, 4.00; Inositol, 100.00; Ascorbic acid, 50.00–250.00; Sucrose, 10000–30000.00; Kinetin, 0.02–4.0; Benzyl amino purine, 0.5–5.0; Agar, 7000.00–12000, all added in weight as milligrams and the final volume made up to one liter by adding water.

Yet another embodiment of the present invention wherein the pH of the said compositions is in the range of 5.4 to 6.2.

Still another embodiment of the present invention, for said compositions wherein at least one plant growth regulator that is employed is selected from the group consisting of auxins and cytokinins, and a combination thereof.

Yet another embodiment of the present invention, the compositions wherein the growth regulator auxin is selected from the group consisting of indole acetic acid, indole butyric acid and naphthalene acetic acid, at a concentration range varying between 0.01 to 10 mg/L w/v.

Still another embodiment of the present invention, the compositions wherein the growth regulator cytokinins is selected from the group consisting of 6-benzylamino-purine, gamma-gamma-dimethyl allylamino purine, isopentinyl adenine and kinetin, at a concentration range varying between 0.01 mg/L up to 20 mg/L.

The present invention also provides a process for producing a composition for inducing organized shoots for micro-propagation of scented *Pandanus amaryllifolius*, said process comprising mixing the following ingredients $NH_4NO_3$, in the range of 750–2000, $KNO_3$, 800–1800; $H_3BO_4$, 6.2; $KH_2PO_4$, 170.0; KI, 0.83; $Na_2MoO_4$, 0.25; $CoCl_2$, 0.025; $CaCl_2$ $2H_2O$, 440–800; $MgSO_4$ $7H_2O$, 370.00; $MnSO_4$ $4H_2O$, 22.30; $MnSO_4$ $4H_2O$, 22.30; $ZnSO_4$, 8.60; $CuSO_4$ $5H_2O$, 0.025; $Na_2$ EDTA, 37.35; $FeSO_4$ $7H_2O$, 27.85; Thiamine HCl, 1.00; Pyridoxine HCl, 1.00; Nicotinic acid, 1.00; Glycine, 4.00; Inositol, 100.00; Ascorbic acid, 50.00–250.00; Glutamine, 50–200; Sucrose, 10000–40000; Soluble polyvinyl pyrrolidone 500–4000; Benzyl amino purine, 0.01–2.0; GELRITE-™ (phytagel), 2000.00 all added in weight as milligrams and the final volume made up to one liter by adding glass distilled water.

The present invention further provides a process for producing a composition for inducing multiple shoots for the micro-propagation of scented *Pandanus amaryllifolius*, said process comprising mixing of the following ingredients:$NH_4NO_3$, in the range of 1000–2500, $KNO_3$, 500–2000; $H_3BO_4$, 6.2; $KH_2PO_4$, 170.0; KI, 0.83; $Na_2MoO_4$, 0.25; $CoCl_2$, 0.025; $CaCl_2$ $2H_2O$, 440.00; $MgSO_4$ $7H_2O$, 370.00; $MnSO_4$ $4H_2O$, 22.30; $MnSO_4$ $4H_2O$, 22.30; $ZnSO_4$, 8.60; $CuSO_4$ $5H_2O$, 0.025; $Na_2$ EDTA, 37.35; $FeSO_4$ $7H_2O$, 27.85; Thiamine HCl, 1.00; Pyridoxine HCl, 1.00; Nicotinic acid, 1.00; Glycine, 4.00; Inositol, 100.00; Ascorbic acid, 50.00–250.00; Sucrose, 10000–30000.00; Kinetin, 0.02–4.0; Benzyl amino purine, 0.5–5.0; Agar, 7000.00–12000, all added in weight as milligrams and the final volume made up to one liter by adding water.

An embodiment of the present invention, wherein for the above processes the pH of the medium is in the range of 5.4 to 6.2.

Another embodiment of the present invention, wherein for the above processes at least one plant growth regulator that is employed in the medium is selected from the group consisting of auxins and cytokinins, and a combination thereof.

Yet another embodiment of the present invention, wherein for the above processes the growth regulator auxin is selected from the group consisting of indole acetic acid, indole butyric acid and naphthalene acetic acid, at a concentration range varying between 0.01 to 10 mg/L w/v.

Still another embodiment of the present invention, wherein for the above processes the growth regulator cytokinins is selected from the group consisting of 6-benzylamino-purine, gamma-gamma-dimethyl allylamino purine, isopentinyl adenine and kinetin, at a concentration range varying between 0.01 mg/L up to 20 mg/L.

The following examples are given by way of illustration of the present invention and therefore, should not be construed to limit the scope of the invention.

EXAMPLE 1

Medium for establishment of aseptic cultures: Shoots from healthy *Pandanus* plants are collected and the 0.5–1.5 cm long shoot axis with lateral/terminal shoot buds are treated to remove bacterial/fungal (contaminants) by dipping the shoot axis in 0.1% w/v of freshly prepared aqueous mercuric chloride solution for 6 minutes followed by several rinses with sterilised distilled water. The meristems/shoot buds are aseptically removed by cutting with sterile scalpel under laminar flow and cultured on a first nutrient medium, namely Murashige and Skoog's medium. This first culture medium is prepared by dissolving in water the following nutrients:

| Constituents | Concentration in medium (milligram/Liter) |
| --- | --- |
| $NH_4NO_3$ | 1650 |
| $KNO_3$ | 1425 |
| $H_3BO_4$ | 6.2 |
| $KH_2PO_4$ | 170.0 |
| KI | 0.83 |
| $Na_2MoO_4$ | 0.25 |

-continued

| Constituents | Concentration in medium (milligram/Liter) |
|---|---|
| $CoCl_2$ | 0.025 |
| $CaCl_2\ 2H_2O$ | 440.00 |
| $MgSO_4\ 7H_2O$ | 370.00 |
| $MnSO_4\ 4H_2O$ | 22.30 |
| $ZnSO_4 7H_2O$ | 8.60 |
| $CuSO_4\ 5H_2O$ | 0.025 |
| $Na_2$ EDTA | 37.35 |
| $FeSO_4\ 7H_2O$ | 27.85 |
| Thiamine HCl | 1.00 |
| Pyridoxine HCl | 1.00 |
| Nicotinic acid | 1.00 |
| Glycine | 4.00 |
| Inositol | 100.00 |
| Sucrose | 30000.00 |
| Glutamine | 100.0 |
| Benzyl amino purine | 0.5 |
| Soluble polyvinyl pyrrolidone | 1000.00 |
| Gelrite | 2000.00 |

The pH of the medium is adjusted to 5.8 prior to adding gelrite and boiled to homogeneity, dispensed to culture bottles and the screw-capped culture bottles with medium are autoclaved at 121 degree C., 15 lb/cm² for 20 minutes. The surface sterilized shoot cuttings are then placed, one at a time using sterile forceps, in a sterile petri-dish in a laminar flow, the shoot tip and small shoot-bud explants are separated from the shoot cuttings with the help of sharp scalpel blades, further appropriately trimmed to obtain small shoot buds of 0.5–2 millimeter size and placed on sterile medium contained in the culture bottles. The shoot buds placed on the sterile nutrient medium are incubated in dark at 25±2 degree C. until tiny shoot cultures are established that may take 4–6 weeks period. In addition to forming tiny shoot buds, there may be a ten-fold multiplication in the number of shoot buds during this treatment. The response of initial explants towards the formation of shoot buds and tiny shoots during this treatment may be up to 10%.

The various other levels and combinations of kinetin and benzyl amino purine and other growth regulators such as 2,4-dichlorophenoxy acetic acid, indole acetic acid, indole butyric acid, added to the nutrient medium, may result in poor response or lesser percentage of response to form shoot cultures or abnormal callus growth without forming shoots.

The medium without any growth regulator or lesser sucrose levels may not support the establishment of shoot cultures from shoot tip/shoot bud explants.

EXAMPLE 2

Medium for multiplication of aseptic shoots: The shoot cultures established as in example 1 has to be used as the explant material for the clonal multiplication of *Pandanus* shoots. The shoot buds established as in Example 1 are removed aseptically in a laminar flow chamber and placed on a sterile petri plate. If there is clustered shoot bud formation, each bud is separated by cutting using sterile scalpel. About three to four shoot buds are then placed on a liquid nutrient medium containing the macroelements, microelements, vitamins and sucrose of Murashige and Skoog medium (MS, 1962, Physiol. Plantarum 15:473–497) are similar to those in Example 1 with the following nutrients in the second medium is prepared by dissolving in water the following nutrients:

| Constituents | Concentration in medium (milligram/Liter) |
|---|---|
| $NH_4NO_3$ | 1650.00 |
| $KNO_3$ | 1425.00 |
| $H_3BO_4$ | 6.2 |
| $KH_2PO_4$ | 170.0 |
| KI | 0.83 |
| $Na_2MoO_4$ | 0.25 |
| $CoCl_2$ | 0.025 |
| $CaCl_2\ 2H_2O$ | 440.00 |
| $MgSO_4\ 7H_2O$ | 370.00 |
| $MnSO_4\ 4\ H_2O$ | 22.30 |
| $ZnSO_4 7H_2O$ | 8.60 |
| $CuSO_4\ 5H_2O$ | 0.025 |
| $Na_2$ EDTA | 37.35 |
| $FeSO_4\ 7H_2O$ | 27.85 |
| Thiamine HCl | 1.00 |
| Pyridoxine HCl | 1.00 |
| Nicotinic acid | 1.00 |
| Glycine | 4.00 |
| Inositol | 100.00 |
| Sucrose | 20000.00 |
| Kinetin | 1.0 |
| Benzyl amino purine | 1.5 |
| Agar-agar | 8000.00 |

The pH of the second medium is adjusted to 5.8 and boiled to homogeneity, dispensed about 40 milliliter to conical flasks and the medium autoclaved at 121 degree C., 15 lb/cm² for 20 minutes.

The shoots are incubated in the second nutrient medium and incubated under a photoperiod of 16 h with an illumination of 2000 lux at 25±2 degree C. for a period of 30–45 days by which time each shoot forms nearly ten additional shoots. The shoots are then separated aseptically, the larger ones are transferred to a third nutrient medium for shoot elongation as well as rooting as in Example 3, and the smaller ones are transferred to the second medium and grown for a period of 3–6 weeks, the process is repeated to obtain a large number of shoots.

EXAMPLE 3

Medium for root induction and partial hardening: The larger shoots of 2–3 cm length multiplied as in Example 2 are transferred to a third medium developed for rooting and partial hardening containing the following nutrients in water:

| Stock | Constituents | Stock solution (grams/liter) | Milliliter volume of stock solution in 1 litre medium |
|---|---|---|---|
| A | $NH_4NO_3$ | 82.5 | 10 |
| B | $KNO_3$ | 95.0 | 10 |
| C | $H_3BO_4$ | 1.24 | 2.5 |
|   | $KH_2PO_4$ | 24.0 | |
|   | KI | 0.166 | |
|   | $Na_2MoO_4$ | 0.55 | |
|   | $CoCl_2$ | 0.005 | |
| D | $CaCl_2\ 2H_2O$ | 88.0 | 2.5 |
| E | $MgSO_4\ 7H_2O$ | 74.0 | 2.5 |
|   | $MnSO_4\ 4H_2O$ | 4.46 | |
|   | $ZnSO_4$ | 1.72 | |
|   | $CuSO_4\ 5H_2O$ | 0.005 | |
| F | $Na_2$ EDIA | 7.4 | 2.5 |
|   | $FeSO_4\ 7H_2O$ | 5.57 | |
| G | Thiamine HCl | 0.2 | 2.5 |
|   | Pyridoxine HCl | 0.2 | |
|   | Nicotinic acid | 0.2 | |

-continued

| Stock | Constituents | Stock solution (grams/liter) | Milliliter volume of stock solution in 1 litre medium |
|---|---|---|---|
| | Glycine | 0.8 | |
| | Sucrose | | 10 g/L |
| | Agar | | 10 g/L |

The plantlets were nurtured for 3 weeks at 25–30° C. under 2000 lux illumination where 100% rooting may be encountered which is accompanied by further growth of shoots. The rooted shoots are removed from the container, washed in running tap water, and then transferred to soil compost containing 1 part of red soil and 2 parts of garden humus, and kept in a place with 90% humidity for another three weeks period. The hardened plantlets may be transferred to green house till they are planted in the field.

The Main Advantages of the Invention
1. The present invention provides, for the first time, a medium formulation that efficiently supports shoot bud establishment to form aseptic shoot cultures of *Pandanus amaryllifolius*.
2. The present invention also provides an efficient process for shoot multiplication allowing 10-fold increase in the shoot number in 4 weeks period, which is a high rate of multiplication using tissue culture technology.
3. The process of the present invention involves a nutrient medium formulation for continuous multiplication of *Pandanus* plants throughout the year.
4. The process of the present invention allows producing *Pandanus amaryllifolius* planting material free from saprophytic, fungal and bacterial diseases.

What is claimed is:

1. A method for the micro-propagation of scented *Pandanus amaryllifolius* through tissue culture, said method comprising the steps of:
   a. cutting one or more explants of *Pandanus amaryllifolius*;
   b. removing any soil and other contaminants from the surface of the explants to yield decontaminated explants;
   c. cutting the decontaminated explants in laminar flow;
   d. culturing the explants for three to eight weeks is at 20–35 degree C. in dark in a medium consisting of following ingredients $NH_4NO_3$, in the ran of 750–2000; $KNO_3$, 800–1800; $H_3BO_4$, 6.2; $KH_2PO_4$, 170.0; KI, 0.83; $Na_2MoO_4$, 0.25; $CoCl_2$, 0.025; $CaCl_2$ $2H_2O$, 440–800; $MgSO_4$ $7H_2O$, 370.00; $MnSO_4$ $4H_2O$, 22.30; $MnSO_4$ $4H_2O$, 22.30; $ZnSO_4$, 8.60; $CuSO_4$ $5H_2O$, 0.025; $Na_2$ EDTA, 37.35; $FeSO_4$ $7H_2O$, 27.85; Thiamine HCl, 1.00; Pyridoxine HCl, 1.00; Nicotinic acid 1.00; Glycine, 4.00; Inositol, 100.00; Ascorbic acid, 50.00–250.00; Glutamine, 50–200; Sucrose, 10000–40000; Soluble polyvinyl pyrrolidone 500–4000; Benzyl amino purine, 0.01–2.0; gellan gum, 2000.00, added in weight as milligrams and the final volume made up to one liter by adding glans distilled water at a pH in the range of 5.4 to 6.2 and sterilized by autoclaving, to obtain organized shoot bud/shoot,
   e. continuing the culture of the explants until organized shoot buds/shoots are formed;
   f. harvesting the shoot buds/shoots thus formed;
   g. culturing the shoots produced in step (f) in a second medium consisting of following ingredients $NH_4NO_3$, in the range of 1000–2500, $KNO_3$, 500–2000; $H_3BO_4$, 6.2; $KH_2PO_4$, 170.0; KI, 0.83; $Na_2MoO_4$, 0.25; $CoCl_2$, 0.025; $CaCl_2$ $2H_2O$, 440.00; $MgSO_4$ $7H_2O$, 370.00; $MnSO_4$ $4H_2O$, 22.30; $MnSO_4$ $4H_2O$ 22.30; $ZnSO_4$, 8.60; $CuSO_4$ $5H_2O$, 0.025; $Na_2$ EDTA, 37.35; $FeSO_4$ $7H_2O$, 27.85; Thiamine HCl, 1.00; Pyridoxine HCl, 1.00; Nicotinic acid, 1.00; Glycine, 4.00 Inositol, 100.00; Ascorbic acid, 50.00–250.00; Sucrose, 10000–30000.00; Kinetin, 0.02–4.0; Benzyl amino purine, 0.5–5.0; Agar, 7000.00–12000, added in weight as milligrams and the final volume made up to one liter by adding glass distilled water at 20–35 degree C. in the presence of cool white light of about 1500–6000 lux of 16 our photoperiod for about three to six weeks, at a pH in the range of 5.4 to 6.2 and sterilized by autoclaving to induce multiple shoots;
   h. transferring the multiple shoots back to the second medium to propagate elongated shoots;
   i. transferring the elongated shoots to a third medium comprising about 50% of the salts of the second medium without growth regulator and 30–80% sucrose of the second medium, all dissolved in tap water, at a pH in the range of 5.4 to 6.2, 10000 mg per liter of agar and sterilized by autoclaving; and
   j. culturing the shoots of step (i) at about 20–35 degree C. in the presence of cool white light of about 1500–6000 lux of 16 hour photoperiod for at least three weeks, to induce roots and to partially harden the individual shoots and further to obtain a large number of partially hardened shoots by tissue culture for transferring to the soil.

2. The method of claim 1, wherein the explants are selected from axillary/terminal shoot tips/buds of the *Pandanus amaryllifolius*.

3. The method of claim 1, wherein at least one plant growth regulator that is employed in the medium of step (d) and step (g) is selected from the group consisting of auxins and cytokinins, and a combination thereof.

4. The method of claim 3, wherein the growth regulator auxin is select from the group consisting of indole acetic acid, indole butyric acid and naphthalene acetic acid, at a concentration range varying between 0.01 to 10 mg/L w/v.

5. The method of claim 3, wherein the growth regulator cytokinins is selected from the group consisting of 6-benzylamino- purine, gamma-gamma-dimethyl allylamino purine, isopentinyl adenine and kinetin, at a concentration range varying between 0.01 mg/L up to 20 mg/L.

6. The method of claim 1, wherein the step of decontaminating explants of step (b) comprises dipping the explants in a solution containing at least one sterilizing agent selected from the group consisting of sodium hypochlorite, calcium hypochlorite, mercuric chloride, and ethyl alcohol.

7. The method of claim 1, wherein said method facilitates shoot multiplication to the extent of 10 fold in about 4 weeks time period.

8. The method of claim 1, wherein said method facilitates production of *Pandanus amaryllifolius* plantlets free from saprophytic, fungal and bacterial diseases.

* * * * *

UNITED STATES PATENT AND TRADEMARK OFFICE
CERTIFICATE OF CORRECTION

PATENT NO. : 6,849,453 B2
DATED : February 1, 2005
INVENTOR(S) : Bhagyalakshmi Neelwarne et al.

It is certified that error appears in the above-identified patent and that said Letters Patent is hereby corrected as shown below:

Column 9,
Line 47, please replace "ran" with -- range --.
Line 59, please replace "liter" with -- litre -- and please replace "glans" with -- glass --.

Column 10,
Line 7, after "$4H_2O$", please insert a -- , --.
Line 10, after "4.00", please insert a -- ; --.
Line 14, please replace "liter" with -- litre --.
Line 17, please replace "our" with -- hour --.
Line 43, please replace "select" with -- selected --.

Signed and Sealed this

Thirteenth Day of September, 2005

JON W. DUDAS
*Director of the United States Patent and Trademark Office*